United States Patent [19]
Gala

[11] Patent Number: 5,426,233
[45] Date of Patent: Jun. 20, 1995

[54] PREPARATION OF CHIRAL HYDROXYKETONES

[75] Inventor: Dinesh Gala, East Brunswick, N.J.

[73] Assignee: Schering Corporation, Kenilworth, N.J.

[21] Appl. No.: 119,151

[22] PCT Filed: Mar. 25, 1992

[86] PCT No.: PCT/US92/02231
§ 371 Date: Sep. 23, 1993
§ 102(e) Date: Sep. 23, 1993

[87] PCT Pub. No.: WO92/17433
PCT Pub. Date: Oct. 15, 1992

[51] Int. Cl.$^6$ .............................................. C07C 45/64
[52] U.S. Cl. .................................... 568/315; 568/336; 568/316
[58] Field of Search ...................... 568/315, 316

[56] References Cited

U.S. PATENT DOCUMENTS

| | | | |
|---|---|---|---|
| 4,613,611 | 9/1986 | Floyd et al. | 514/443 |
| 4,613,611 | 9/1986 | Middleton et al. | 514/433 |

FOREIGN PATENT DOCUMENTS

| | | | |
|---|---|---|---|
| 0332387 | 9/1989 | European Pat. Off. | C07D 249/08 |
| 421210 | 4/1991 | European Pat. Off. | 568/335 |
| 1569165 | 5/1969 | France | C07C 49/76 |

OTHER PUBLICATIONS

Davis et al, J. Org. Chem., vol. 49, pp. 3241–3243 (1984).
Davis et al, J. Org. Chem., vol. 51, pp. 4083–4085 (1986).
Davis et al, J. Org. Chem., vol. 55, pp. 3715–3717 (1990).
Davis et al, J. Org. Chem, vol. 56, pp. 1143–1145 (1991).
Theodora W. Greene, Protective Groups in Organic Synthesis, John Wiley and Sons, New York, N.Y. (1981). Chapter 2: pp. 10–22.
Franklin A. Davis, et al. J. Org. Chem. vol. 54, pp. 2021–2024 (1989).
Franklin A. Davis, et al., J.A.C.S. vol. 112, pp. 6679–6690 (1990).
Franklin A. Davis et al., Tetrahedron Letter vol. 1989, pp. 779–782 (1982).

*Primary Examiner*—James H. Reamer
*Attorney, Agent, or Firm*—Joseph T. Majka; Edward H. Mazer

[57] ABSTRACT

A process for preparing an hydroxyketone of the formula (X):

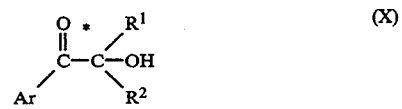

wherein Ar represents substituted phenyl, aromatic heterocyclic, or substituted aromatic heterocyclic; $R^1$ and $R^2$ independently represents hydrogen, C-1 to C-16 alkyl, aromatic, substituted aromatic, aromatic heterocyclic, substituted aromatic heterocyclic or C-1 to C-5 alkyl covalently bonded to Ar, with the provision that $R^1$ and $R^2$ are different. The process comprises contacting a compound of the formula (V):

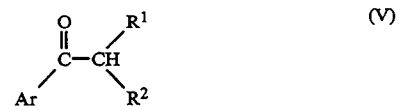

with a solvent, a base and a chiral hydroxylating agent at a temperature of about −85° C. or less.

Compounds of the formulae

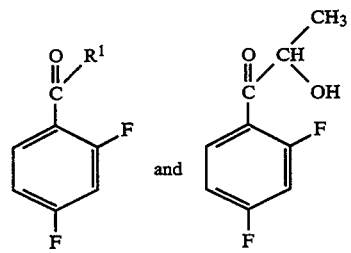

also are disclosed.

6 Claims, No Drawings

PREPARATION OF CHIRAL HYDROXYKETONES

BACKGROUND

Chiral hydroxyketones are useful intermediates for preparing various pharmaceutical compounds, such as anti-fungal reagents. Franklin A. Davis and M. Serajul Haque, J. Org. Chem. 1986, 51, pp. 4083–4085 describe the asymmetric oxidation at −78° C. of the sodium enolates of ketones using chiral (camphorylsulfonyl)oxaziridines to give α-hydroxy ketones. Franklin A. Davis and Michael C. Weismiller, J. Org. Chem., Vol. 55, No. 12, 1990 pp. 3715–3717, reported the preparation of (S)-2-hydroxy-1-phenyl-1-propanone in greater than 95% enantiomeric excess (ee) and 61% yield by oxidation of the sodium enolate of the propiophenone at −78° C. by (+)-((8,8-dichlorocamphoryl)sulfonyl)oxaziridine. Franklin A. Davis et al. J. Org. Chem., 1991. Vol 56, pp 1143–1145 discloses asymmetric hydroxylation with (+)-{(8,8 dimethoxycamphoryl)sulfonyl} sulfonyloxaziridine. None of these references disclose the use of temperatures lower than −78° C. It would be desirable to provide a process for preparing chiral hydroxyketones and salts thereof, in as high or even greater yields and chirality than processes previously taught. It would also be desirable to provide a process for preparing hydroxyketones in which the oxidant (i.e., hydroxylating agent) can be readily recycled in order to reduce operating expenses associated with disposal of the oxidizing agent.

SUMMARY OF THE INVENTION

The present invention is directed toward a process for preparing an hydroxyketone of the formula (X) where $R^1$ and $R^2$ are different:

wherein Ar represents substituted aromatic, substituted aromatic, aromatic heterocyclic, or substituted aromatic heterocyclic; $R^1$ and $R^2$ independently represent hydrogen, C-1 to C-16 alkyl, or aromatic, aromatic heterocyclic or substituted aromatic heterocyclic or C-1 to C-5 alkyl bonded to the Ar. The process comprises contacting a compound of the formula (V):

with a solvent, a base and a chiral hydroxylating agent at a temperature of about −85° C. or less. More preferably, the reaction is carded out at a temperature ranging from about −85° C. to about −120° C., more preferably from about −90° C. to about −110° C., most preferably at about −95° C. In a preferred embodiment, the hydroxyketone is reacted to form a protecting group with the hydroxy moiety.

The present invention is also directed to novel intermediates of the formulae:

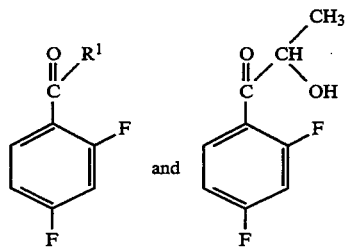

wherein $R^1$ is alkyl, preferably ethyl.

The present invention has the advantage of providing an efficient process for preparing chiral hydroxyketones and salts thereof, in as high or even greater yields and chirality than by processes previously taught. The present invention also has the advantage of providing a process for preparing chiral hydroxyketones which permits selection of the desired stereochemistry (i.e., R or S stereoisomer) of the hydroxyketone by selection of the appropriate starting materials aforehand. The present invention has the further advantage of providing a process for preparing hydroxyketones in which the oxidant can be readily recycled in order to reduce operating expenses associated with disposal of the oxidizing agent.

DETAILED DESCRIPTION OF THE EMBODIMENTS

When utilized herein the terms listed hereinbelow, unless otherwise indicated are defined as follows:

alkyl—comprise straight or branched saturated hydrocarbon moieties (i.e., hydrocarbons having carbon-carbon single bonds) containing from 1 to 16 carbon atoms, preferably from 1 to 6 carbon atoms, such as for example, methyl, ethyl, propyl, isopropyl, butyl, isobutyl, tertbutyl, pentyl, hexyl and the like.

-aromatic—comprises 1 to 3 unsaturated fused ring moieties such as phenyl, naphthyl etc. having from 4 to 14 carbon atoms.

aromatic heterocyclic—cyclic groups having at least one O, S and/or N heteroatom interrupting the ring structure and having a sufficient number of unsaturated carbon to carbon bonds, nitrogen to carbon bonds, etc., to provide aromatic character, with the aromatic heterocyclic groups preferably containing from 4 to 14 carbon atoms, e.g., pyridyl, furyl, thienyl, thiazolyl, imidazolyl, pyrimidinyl, pyrazinyl, pyridazinyl, 1,2,4-triazinyl, benzofuranyl, indolyl, pyrazolyl, oxazolyl, etc. Many times such heterocyclic groups can be bonded via various positions on the ring and all such variations are contemplated, e.g., 2- or 3-furanyl, 2-, 3- or 4-pyridyl, or 2- or 3- pyridyl convalently bonded to alkyl (i.e., $R^1$ or $R^2$) of one to five carbon atoms, etc.

substituted aromatic- phenyl or naphthyl, etc., substituted with one to five of the following groups: alkyl, halo (including chloro, bromo and fluoro), alkoxy of one to 16 carbon atoms, cyano and nitro, such as 2,4-difluoro, 4-cyano, 2,4-dichloro, 3fluoro, 3-chloro, or 2- or 3-phenyl convalently bonded to alkyl (, i.e., $R^1$ or $R^2$) of one to five carbon atoms, etc. and the like.

The star "*" designates the chiral atom in the hydroxyketone (X). The processes of the present invention can be illustrated as follows, wherein Ar, $R^1$ and $R^2$ are as defined hereinbefore and P is a hydroxy protecting-group:

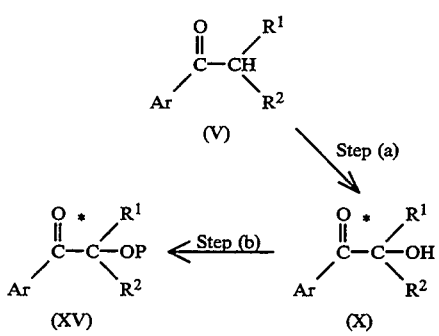

In step (a) compound (V) is contacted with a solvent, a base and a chiral hydroxylating agent at a temperature of about −85° C. or less. Suitable solvents can include aprotic solvents such as ethers, C-5 to C-16 aliphatic hydrocarbons such as pentane, cyclopentane, hexane, cyclohexane; aromatic hydrocarbons such as benzene, toluene, xylenes, etc., and other solvents such as dimethylsulfoxide (DMSO), dimethylformamide (DMF) and tetrahydrofuran (THF), or mixtures of any of the above solvents.

Suitable bases can include the organo-alkali metals such as primary, secondary and tertiary butyl lithiums, such as lithium diisopropyl amide, lithium hexamethyldisilazane, sodium hexamethyldisilazane and potassium hexamethyldisilazane; bases of alkali and alkaline earth metals including carbonates such as sodium, potassium and cesium carbonates; hydroxides such as sodium and potassium hydroxides; hydrides such as sodium, lithium or potassium hydrides; sodium t-butoxide, sodium amylate, sodium methoxide or sodium isopropoxide. The base should be employed in amounts ranging from about 0.9 to about 2 moles base per mole compound (V), preferably from about 0.9 to about 1.3 moles base per mole of compound (V), more preferably from about 1.05 to about 1.1 moles base per mole of compound (V).

Suitable hydroxylating reagents include, but are not limited to, oxaziridines such as (+)-(2R,8aS)(camphorylsulfonyl)oxaziridine, (−)-(2S,8aR)-(camphorylsulfonyl)oxaziridine, (−)-(S,S)-oxaziridine and (+)-((8,8-dichlorocamphoryl)sulfonyl)oxaziridine, (−)-((8,8-dichlorocamphoryl)sulfonyl) oxaziridine such as described in Franklin A. Davis and M. Serajul Haque, and Franklin A. Davis and Michael C. Weismiller, supra, or (+)-{(8,8dimethoxycamphoryl)sulfonyl}oxaziridine, (−)-{(8,8-dimethoxycamphoryl)sulfonyl}oxaziridine as disclosed in Davis, et al., supra. Generally, the hydroxylating agent is employed in amounts effective to accomplish hydroxylation to the degree of completion desired. Such amounts can range from about 0.9 to about 50 moles or more of the hydroxylating agent per mole of compound (V), preferably from about 0.9 to about 4 moles hydroxylating agent, more preferably from about 0.9 to about 1.5 moles of hydroxylating agent.

The present process can be carded out at a temperature of about −85° C. or less. More preferably, the reaction is carried out at a temperature ranging from about −90° C. to about −120° C., more preferably from about −90° to about −110° C., most preferably at about −95° C. The reactants are preferably stirred or agitated until the desired extent of completion of the reaction is attained. Such times can range from about one-half hour to about 24 hours or more, preferably from about one to about 8 hours, as evaluated by any suitable procedure, ie. thin-layer chromatograph (TLC), high performance liquid chromatography (HPLC), gas chromatograph (GC), infrared spectometry (IR) or nuclear magnetic resonance spectrometry (NMR).

The desired hydroxyketone (X) can be recovered by quenching the reaction mixture with a proton source such as aqueous ammonium chloride, aqueous ammonium iodide, with mineral acids such as hydrochloric or sulfuric, or organic acids such as acetic, propanoic, oxalic; or with buffers such as phosphate and acetate buffers, and the like. The quenching can be conducted at temperatures ranging from about −100° C. to about room temperature, preferably from about −40° to about −90° C., more preferably from about −65° to about −80° C. Hydroxyketone (X) can be recovered by separating the organic layer from the aqueous layer and by removing the organic solvent by conventional procedures such as by distillation, evaporation, filtration, chromatography and the like.

In the present process, the order of addition of the reactants is not critical, although preferably compound (V) is mixed with the solvent and base, followed by addition of the hydroxylating agent, then the quenching reagent. Alternatively, through less preferably, compound (V) can be contacted with solvent and the hydroxylating agent, followed by addition of the base, then the quenching reagent.

Optionally, step(a) can be carried out in the presence of a phase transfer catalyst. A phase transfer catalyst is a material which catalyzes a reaction by the transfer of one phase to another. Phase transfer catalysts can include the quaternary ammonium and phosphonium salts, ethers and tertiary amines, as described in U.S. Pat. No. 4,701,531.

In another embodiment of the invention, the spent (ie. used) hydroxylating agent can be recovered by separating the hydroxylating agent from the reaction mixture by chromatography or extraction, preferably by extraction and by regenerating the spent hydroxylating agent. The spent hydroxylating agent can be regenerated by contacting it with an oxidizing reagent such as m-chloroperbenzoic acid (m-CPBA) as taught in Davis and Wesimiller, supra.

In Step (b), hydroxyketone (X) can be contacted with any compound capable of forming a hydroxy protecting group (P) in order to protect the hydroxy moiety. Suitable protecting agents include dihydrofuranyl ether, dihydropyranyl ether, alkoxyalkyl or alkylthioalkyl ether unsaturated or halo derivatives (such as vinyl alkyl ether or a chlor-alkyl alkyl ether), halo-trisubstituted silyl ethers and the like. A preferred protecting agent is dihydropyranyl ether. Optionally, the protecting group can be prepared in the presence of aprotic solvents such as those described hereinbefore, or with other solvents such as chloroform, carbon tetrachloride, toluene, methylene chloride or ethyl acetate. A catalyst can also optionally be employed, such as phosphorous oxychloride ($POCl_3$), phosphorous pentachloride ($PCl_5$), acetic acid, amberlyst, most preferably para-toluene sulfonic acid (PTSA) or pyridinium para-toluene sulfonic acid (PPTS). The catalyst should be able to facilitate the reaction and minimize epimerization and degradation of hydroxyketone (X). The formation of such protecting groups is known. See for example, Theodora W. Greene, Protective Groups in Organic Synthesis, John Wiley and Sons, New York, N.Y., (1981), Chapter 2: Protection of the Hydroxyl Group Including 1,2- and 1,3-Diols, pp. 10–22.

The protected hydroxyketone (XV) can serve as a protected intermediate for preparing chemically pure, enantiomeric compounds having antifungal activity, as described in Patent Cooperation Treaty (PCT) patent publication no. WO91/03451 published Mar. 21, 1990.

PREPARATION OF STARTING MATERIALS

The starting materials of compound (V) can be prepared by known procedures, such as described in The Merck Index, 9th Edition, 1976, p. ONR-33 by the Friedel-Crafts reaction:

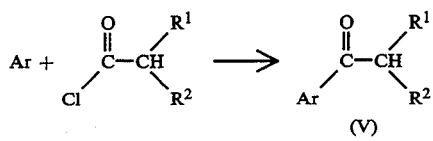

Generally, the phenyl or aromatic heterocylic compound is reacted with an acid chloride or anhydride in the presence of a Lewis acid such as $AlCl_3$, $BF_3$, $TiCl_4$, $SnCl_4$ or $FeCl_3$. The acylated product is recovered via extraction or chromatographic separation procedures.

The following preparative example is presented to exemplify an embodiment of the preparation of the starting materials, but as such, is not to be considered limiting the overall scope of the same.

Preparative Example 1. 2′,4′-difluoropropiophenone

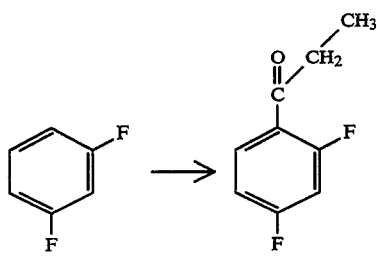

Stir 50 g (0.43 mole) of difluorobenzene and 76 g (0.56 mole) of aluminum chloride ($AlCl_3$)in a 500 ml round bottom three-neck flask. Add dropwise 49 ml (52 g; 0.56 mole) of propionyl chloride. Stir the reaction mixture for 30 min at room temperature. Warm the reaction mixture in an oil bath to a temperature of 45° C. and let stir overnight. Work up by the addition of ether and wash with water, saturated sodium bicarbonate (NaHCO$_3$), water, and saturated sodium chloride (NaCl). Dry over magnesium sulfate (MgSO$_4$) and concentrate to give 68 g crude product, which is distilled under a vacuum of 0.3 millimeters mercury at a distillation temperature of 50°–52.5° C. to give 51.1 g (82% yield) of title compound, a liquid.

Calculated for $C_9H_8OF_2$: C, 63.53; H, 4.74; F, 22.3. Analyzed: C, 59.82; H, 4.29; F, 21.9.

The following examples are presented to exemplify an embodiment of the present invention, but as such, are not to be considered limiting the overall scope of the same.

EXAMPLE 1

Preparation of 1-(2,4-difluorophenyl)-2(R)-hydroxypropanone

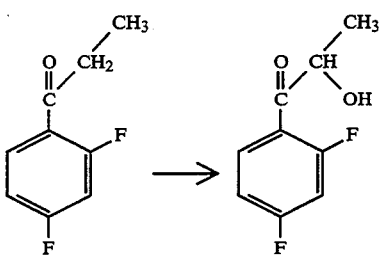

A stirred solution of 14.28 g (0.084 mole) of 2′,4′-difluoropropiophenone, in 800 milliliters (ml) dry THF under nitrogen (N$_2$) is cooled to a temperature of −65° C. and 97 ml (0.096 mole) of sodium hexamethyldisilazane (NaHMDS) in THF is slowly added maintaining the temperature between −60° to −65° C. The stirred solution is cooled to −95° C. To the solution 40 g (0.13 mole) of (−)-((8,8dichlorocamphoryl)sulfonyl)oxaziridine is added in batches maintaining the temperature between −90° to −95° C. The reaction mixture is stirred for two hours and allowed to warm up to about −60° C. The reaction is quenched with 300 ml saturated aqueous NH$_4$Cl solution with vigorous stirring. When this mixture reaches room temperature, the organic layer is separated and the aqueous layer is extracted with 200 ml of THF/ether (95:5 volume/volume), followed by 200 ml of THF/ether (1:1 ). The combined organic portions are washed with 400 ml saturated aqueous NaCl solution, dried over anhydrous sodium sulfate (Na$_2$SO$_4$) and magnesium sulfate (MgSO$_4$) and concentrated to give 57 g of crude product, a tan-white semi-solid. This semi-solid is extracted with 5×200 ml portions of petroleum ether, the extracts are combined and concentrated to a constant weight under vacuum to obtain 15.3 g (85% yield) of a tan oil. Chiral HPLC indicates the title product has an enantiomeric ratio (R:S) of 94.3:5.7, with an enantiomeric excess (major enantiomer less minor enantiomer) of 88.6%. Of the solid separated by filtration, 37.8 g is the spent hydroxylating reagent, which is oxidized to oxaziridine with m-chloroperbenzoic acid as described by Davis and Weismiller, supra.

EXAMPLE 2

Preparation of Tetrahydropyranyl protected 1-(2,4-difluorophenyl)-2(R)-hydroxypropanone

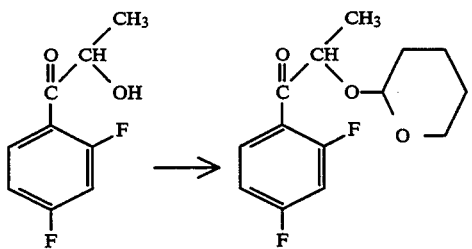

To a stirred mixture of 13 g (0.067 mole) of the α-hydroxyketone from Example 1 and 8.6 ml (0.092 mole) dihydropyran, add 1.4 g of pyridinium p-toluene sulfonate. Stir the reaction mixture at 35° to 38° C. for 4 hr followed by stirring at 40° to 42° C. for an additional 0.5hr until the starting material is consumed. Remove the volatiles under vacuum. Dilute the mixture with ether, wash with water followed by brine, dry over anhydrous Na$_2$SO$_4$ and MgSO$_4$ and concentrate the organic layer under vacuum to obtain 20.4 g (quantitative) of title compound.

EXAMPLE 3.

Effect of temperature on the chiral hydroxylation of 2′,4′-difluoropropiophenone to 1-(2,4-difluorophenyl)-2(R)-hydroxy-propanone with different hydroxylating reagents

| Hydroxylating reagent | Temperature °C. | Yield % | Enantiomer Ratio (R:S) | Enantiomeric Excess (ee) |
|---|---|---|---|---|
| (−)-(camphoryl- sulfonyl)- oxaziridine | −78 | 80 | 75:25 | 50 |
|  | −85 to −90 | 80 | 85:15 | 70 |
| (−)-((8,8- dichlorocamphoryl)- sulfonyl)oxaziridine | −78 | 80 | 90:10 | 80 |
|  | −85 to −90 | 80 | 94:6 | 88 |

What is claimed is:

1. A process for preparing an hydroxyketone of formula (X) where R$^1$ and R$^2$ are different:

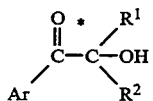

wherein Ar represents dihalophenyl; R$^1$ and R$^2$ independently represent hydrogen or a C$_1$-C$_6$ alkyl comprising:
contacting a compound of formula (V):

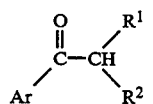

with a solvent, a base and a chiral hydroxylating agent, selected from the group consisting of (−)-(camphorylsulfony)-oxaziridine and (−)-((8.8-dichlorocamphoryl)sulfonyl)oxaziridine at a temperature of −85° C. or less.

2. The process of claim 1 further characterized by compound (V) representing 2′,4′-difluoro-propiophenone and compound (X) representing 1-(2,4-difluorophenyl)-2(R)-hydroxy-propanone.

3. The process of claim 1 further characterized by the reaction temperature ranging from about −90° C. to about −120° C.

4. The process of claim 1 further characterized by the solvent being tetrahydrofuran and the base being sodium hexamethyldisilazane.

5. The process of any of claim 1 further characterized by the chiral hydroxylating reagent being an oxaziridine.

6. The process of any of claims 1 further characterized by contacting hydroxyketone (X) with a compound capable of forming a hydroxy protecting group in order to protect the hydroxy moiety.

* * * * *